US008455228B2

(12) United States Patent
Jaroszeski et al.

(10) Patent No.: US 8,455,228 B2
(45) Date of Patent: Jun. 4, 2013

(54) METHOD TO FACILITATE DIRECTED DELIVERY AND ELECTROPORATION USING A CHARGED STREAM

(75) Inventors: Mark Jaroszeski, Wesley Chapel, FL (US); Gabriel A. Lopez-Diaz, Wesley Chapel, FL (US); Richard J. Connolly, Riverview, FL (US); Andrew M. Hoff, Tampa, FL (US)

(73) Assignee: University of South Florida, Tampa, FL (US)

( * ) Notice: Subject to any disclaimer, the term of this patent is extended or adjusted under 35 U.S.C. 154(b) by 925 days.

(21) Appl. No.: 12/207,846

(22) Filed: Sep. 10, 2008

(65) Prior Publication Data

US 2009/0004717 A1 Jan. 1, 2009

Related U.S. Application Data

(63) Continuation of application No. 11/306,945, filed on Jan. 17, 2006, now abandoned, which is a continuation of application No. PCT/US2004/023052, filed on Jul. 16, 2004.

(60) Provisional application No. 60/971,103, filed on Sep. 10, 2007, provisional application No. 61/084,118, filed on Jul. 28, 2008, provisional application No. 61/086,962, filed on Aug. 7, 2008, provisional application No. 60/481,086, filed on Jul. 16, 2003.

(51) Int. Cl.
*C12N 13/00* (2006.01)

(52) U.S. Cl.
USPC ............... 435/173.6; 435/173.2; 435/173.4; 435/173.5

(58) Field of Classification Search
USPC ................ 435/173.1, 173.4–173.6
See application file for complete search history.

(56) References Cited

U.S. PATENT DOCUMENTS 5,019,034 A * 5/1991 Weaver et al. .................. 604/20
6,780,178 B2 * 8/2004 Palanker et al. ................ 606/34
6,929,949 B1 8/2005 Hoff et al.

(Continued)

FOREIGN PATENT DOCUMENTS

WO 02/064767 * 8/2002

OTHER PUBLICATIONS

Yasuhiro Ogawa, Noriyuki Morikawa, Akiko Ohkubo-Suzuki, Sousuke Miyoshi, Hiroyuki Arakawa, Yasuhiro Kita, Shintaro Nishimura. "An epoch-making application of discharge plasma phenomenon to gene-transfer." Biotechnology and Bioengineering. vol. 92. Issue 7. Sep. 16, 2005. pp. 865-870.

(Continued)

*Primary Examiner* — Melanie Y Brown
(74) *Attorney, Agent, or Firm* — Michele L. Lawson; Smith & Hopen, P.A.

(57) ABSTRACT

A method for facilitating a delivery of a molecule into an interior space of a cell includes the steps of introducing a molecule into a biological structure comprising a cell and applying a substantially continuous low-level electric field, in the form of non-thermal plasma (ionized gas) generated by a direct current voltage applied to an electrode, to the molecule and biological structure. The field is applied for a duration sufficient to effect a change in porosity the cell of the biological structure sufficient to facilitate an entry of a desired molecule into an interior thereof.

34 Claims, 7 Drawing Sheets

U.S. PATENT DOCUMENTS

| | | | |
|---|---|---|---|
| 7,341,864 B2* | 3/2008 | Sakamoto et al. | 435/285.2 |
| 7,402,435 B2* | 7/2008 | Miyoshi et al. | 435/455 |
| 2002/0074221 A1* | 6/2002 | Mallinson et al. | 204/170 |
| 2003/0018295 A1* | 1/2003 | Henley et al. | 604/20 |
| 2004/0023394 A1* | 2/2004 | Orwar et al. | 435/461 |
| 2004/0193097 A1* | 9/2004 | Hofmann et al. | 604/20 |
| 2006/0260003 A1 | 11/2006 | Gilbert et al. | |
| 2008/0033340 A1 | 2/2008 | Heller et al. | |
| 2009/0318846 A1* | 12/2009 | Prausnitz et al. | 604/20 |

OTHER PUBLICATIONS

Ingrid E. Kieft, Delphine Darios, Anton J. M. Roks, and Eva Stoffels. "Plasma Treatment of Mammalian Vascular Cells: A Quantitative Description." IEEE Transactions of Plasma Science. vol. 33. No. 2. Apr. 2005. pp. 771-775.

Thomas W. Chalberg, Alexander Vankov, Fanni E. Molnar, Alexander F. Bitterwick, Philip Huie, Michele P. Calos, and Daniel V. Palanker. "Gene Transfer to Rabbit Retina with Electron Avalanche Transfection." Investigative Ophthalmology and Visual Science. 2006. vol. 47. pp. 4083-4090.

I.E. Kieft, J.L.V. Broers, V. Caubet-Hilloutou, D.W. Slaaf, F.C.S. Ramaekers, E. Stoffels. "Electric discharge plasmas influence attachment of cultured CHO K1 cells." Bioelectromagnetics. vol. 25. Issue 5. Jun. 9, 2004. pp. 362-368.

Roppei Yamadaa, Syunsuke Yanomac, Makoto Akaikeb, Akira Tsuburayab, Yukio Sugimasab, Shoji Takemiyab, Hisahiko Motohashib, Yasushi Rinoa, Yoshinori Takanashia and Toshio Imadaa. "Water-generated negative air ions activate NK cell and inhibit carcinogenesis in mice." Cancer Letters. vol. 239. Issue 2. Aug. 8, 2006. pp. 90-197.

E Stoffels, I E Kieft and R E J Sladek. "Superficial treatment of mammalian cells using plasma needle." J. Phys. D: Appl. Phys. vol. 36. 2003. pp. 2908-2913.

T. Vilaithong, L. D. Yu, P. Apavatjrut, B. Phanchaisri, S. Sangyuenyongpipat, S. Anuntalabhochai and I. G. Brown. "Heavy ion induced DNA transfer in biological cells." Radiation Physics and Chemistry. vol. 71. Issues 3-4. Oct.-Nov. 2004. pp. 927-935.

Zengliang Yu. "Ion beam application in genetic modification." Plasma Science. IEEE. vol. 28. Issue 1. Feb. 2000. pp. 128-132.

Electrical Engineering Handbook, Edited by Richard C. Dorf, 1997, CRC Press, 2nd ed., p. 523.

Fridman, G., Shereshevsky, A., Jost, M. M., Brooks, A. D., Fridman, A., Gutsol, A., Vasilets, V., Friedman, G., Floating Electrode Dielectric Barrier Discharge Plasma in Air Promoting Apoptotic Behavior in Melanoma Skin Cancer Cell Lines, Plasma Chem Plasma Process (2007) 27:163-176.

Ogawa, Y., Morikawa, N., Ohkubo-Suzuki, A., Miyoshi, S., Arakawa, H., Kita, Y., Nishimura, S., An Epoch-Making Application of Discharge Plasma Phenomenon to Gene-Transfer, Biotechnology and Bioengineering (2005) vol. 92, No. 7:865-870.

* cited by examiner

METHOD TO FACILITATE DIRECTED DELIVERY AND ELECTROPORATION USING A CHARGED STREAM

CROSS REFERENCE TO RELATED APPLICATIONS

This application claims priority to U.S. Provisional Application No. 60/971,103, filed Sep. 10, 2007; U.S. Provisional Application No. 61/084,118, filed Jul. 28, 2008; and U.S. Provisional Application No. 61/086,962, filed Aug. 7, 2008. This application is also a continuation-in-part of U.S. patent application Ser. No. 11/306,945, filed Jan. 17, 2006, which application is a continuation of PCT Patent Application No. PCT/US2004/23052 filed Jul. 16, 2004, which application claims priority to U.S. Provisional Application No. 60/481,086, filed Jul. 16, 2003.

FIELD OF INVENTION

This invention relates to the use of an electric field to affect the delivery of a molecule to a target tissue site and facilitate the uptake of a molecule by a cell.

BACKGROUND OF THE INVENTION

There are various electroporation applicators and methods of use known in the art. The prior art methods involve two independent procedures, the introduction of a target molecule into a target tissue and the subsequent electroporation of the target tissue to induce electroporation. The majority of prior art methods require two separate devices, one to introduce the target molecule and a second to provide for the electroporation of the target tissue site.

Prior art methods to introduce a target molecule into a target tissue include the use of intrusive instruments or the application of an electric field using devices that must directly contact the skin with the stated purpose of altering the skin to allow a drug to move through the external skin barrier.

The delivery of molecules by electroporation in vivo is typically, but not necessarily, carried out by first exposing the cells (located within a tissue) of interest to the molecule to be delivered. This is accomplished by placing the molecules of interest into the extracellular space by injection, jet injection, transdermal delivery, infusion into tissue or blood vessel, or other means known in the art. The cells are then exposed to electric fields by administering one or more direct current pulses. Pulsed electric fields are normally applied using an electrical generator and electrodes that contact or penetrate a region of tissue, which allows electrical energy to be transmitted to the cells of interest. Electrical treatment is typically, but not necessarily, conducted in a manner that results in a temporary cell membrane destabilization with minimal cytotoxicity.

The intensity of electrical treatment is described by the magnitude of the applied electric field. This field is defined as the voltage applied to the electrodes divided by the distance between the electrodes. Generally, electric field strengths ranging from 100 to 5000V/cm have been used; this range has been dictated by the need to interfere with the cell membrane to effect the uptake of the molecular species desired. In addition, the field strength required for delivery is also a function of the type of tissue to be treated, with some requiring higher fields owing to their specific natures.

High field strengths, 100V/cm and greater, were used exclusively in the past. The duration of the applied fields is also an important factor, and the relationship between field strength and duration is critical. The current state of the art utilizes high electric field strengths to effect the membrane change and requires pulse durations that are very brief in order to achieve molecular delivery. The concept of very long pulse durations (greater than 100 ms) has heretofore never been used with respect to the field strength, enabling in vivo molecular delivery using almost insignificant electric fields. In fact, the converse was held to be true by practitioners of the art; operating parameters with short-duration high fields being held as the only way to achieve electroporation. The pulsed electric fields used for molecule delivery are generally rectangular in shape; however, exponentially decaying pulses and bipolar pulses have also been used. Molecular loading has been performed with pulse widths ranging from microseconds to milliseconds. The number of pulses delivered typically has ranged from one to eight, with multiple pulses being applied during the course of a treatment.

Accordingly, there is a need in the art for a method and apparatus to facilitate the directed delivery and subsequent electroporation of a target molecule in-vivo without the associated pain, muscle contraction, and cell damage associated with direct-contact electroporation applicators.

SUMMARY OF INVENTION

In a first embodiment, the present invention provides a method and apparatus to facilitate the directed delivery and subsequent electroporation of a target molecule in-vivo. An apparatus in accordance with this embodiment includes a reservoir having an electrically conductive top end cap and a micro-porous bottom end cap. The bottom end cap further includes at least one electroporation applicator. To electrically isolate the electrically conductive top end cap from the sidewalls of the reservoir, the apparatus includes an electrical insulator positioned between the underside of the top cap edge and the exterior sidewall of the reservoir. As such, when a voltage from a polarization supply voltage in circuit communication with the top end cap is applied, the reservoir is electrically isolated from the top end cap.

The bottom end cap of the reservoir is micro-porous and may include a micro-porous membrane. Additionally, at least one electroporation applicator is embedded in the micro-porous membrane or otherwise secured to the bottom end cap of the reservoir. Accordingly, the bottom end cap is adapted to be positioned in contact with a target tissue and the electroporation applicators are non-penetrating in nature.

It is within the scope of this embodiment to have a plurality of electroporation applicators embedded in the micro-porous membrane of the bottom end cap. Each of the plurality of electroporation applicators are in circuit communication with an electroporation supply voltage. Because the electroporation mechanism is contained within the device, the tissue damage and pain associated with direct-contact applicators is avoided. The applicators, which provide the electroporation voltage to induce electroporation, are kept away from direct contact with the target cell/tissue by the membrane of the bottom end cap.

The reservoir is adapted to contain a charged entity, or target molecule, to be transported and subsequently electroporated into the target tissue. As such, the reservoir may be non-conductive and fluid tight as required. A variety of target molecules are envisioned by the present invention, including a protein, a plasmid and a therapeutic drug.

In another embodiment, the invention includes a method for molecular delivery and electroporation, the method includes containing a target molecule or charged entity within a reservoir, contacting a micro-porous bottom end cap of the reservoir to a surface of a cellular tissue, applying a polarization voltage to a conductive top end cap of the reservoir adapted to transport the target molecule through the micro-porous bottom end cap of the reservoir and diffuse the target molecule across the surface of the cellular tissue, and applying an electroporation voltage to at least one electroporation applicator positioned on the micro-porous bottom end cap to introduce the target molecule into the interior of a cell of the cellular tissue.

In yet another embodiment, the invention includes a method for facilitating a delivery of a molecule into an interior space of a cell including introducing a molecule to a target tissue comprising a cell and applying a substantially continuous, non-contact electric field to the target tissue. The field is applied for a duration sufficient to effect a change in porosity in the cell of the target tissue sufficient to facilitate an entry of a desired molecule into an interior of the cell.

A device for use with the inventive method includes a hollow tube connected to an ion source, such as a pressurized fluid, on one end and at least one electrode on the opposite end. Gas flowing through the tube passes past the electrode which creates the charged particles (which comprise the electric field). The charged particles then travel to the delivery site. In one embodiment, the electrode is an annular electrode. In another embodiment, the device is also used with a grounding structure, such as a ring constructed from a conductive material. The grounding structure is connected to ground through a conductive wire, which may travel through a high impedance. The grounding structure can be applied to the biological structure directly or, in the case of biological samples, can be used in conjunction with a sample plate. The sample plate of this embodiment further includes an inner chamber and an outer chamber. The inner chamber is disposed to house the sample with the grounding structure is place in the outer chamber.

In a preferred embodiment, the substantially continuous, non-contact and low-level electric field is generated by the deposition of ionized molecules onto target tissues. Depositing ions on the target tissue for an extended period of time leads to charge accumulation, causing an electric potential to be established The elevated electric potential provides the same effects as direct-contact electroporation without the deleterious effects caused by electrodes.

The method of a specific embodiment for facilitating a delivery of a molecule into an interior space of a cell includes the steps of introducing a molecule into a biological structure comprising a cell and applying a substantially continuous low-level electric field, in the form of non-thermal plasma (ionized gas) generated by a direct current voltage applied to an electrode, to the molecule and biological structure. The field is applied for a duration sufficient to effect a change in porosity the cell of the biological structure sufficient to facilitate an entry of a desired molecule into an interior thereof.

The electroporation applicators of the present invention are non-intrusive, therefore the method does not discomfort the patent. In addition to avoiding cellular damage, the embodiments described above overcome the problem in the prior art of insuring that the application of the electroporation treatment is taking place at the same location in the tissue where the molecule was inserted. Due to the time delay caused by the additional step in the prior of placing the electroporation applicators, the injected molecule may have moved from the injection site and therefore the effectiveness of the electroporation effect is greatly reduced. Since the electroporation applicators are an integral component of the present invention, the delivered molecules are assured to be within the electroporation applicators electric field of influence during the treatment procedure. An additional benefit of the present invention is the ability to apply multiple treatments to the same area of tissue without the need to reposition the direct-contact electroporation applicators of the transport mechanism.

BRIEF DESCRIPTION OF THE DRAWINGS

For a fuller understanding of the invention, reference should be made to the following detailed description, taken in connection with the accompanying drawings, in which:

FIG. 1 is an illustrative side view of the apparatus in accordance with one embodiment of the present invention.

FIG. 2A is an illustrated perspective view of a second embodiment of the present invention.

FIG. 2B is a perspective view of an additional device for use with the embodiment of FIG. 2A.

FIG. 3A. Mean normalized fluorescence of B16-F10 cells after plasma mediated delivery of the nonpermeant nucleic acid stain SYTOX-Green.

FIG. 3B. Mean normalized fluorescence of HACAT cells after plasma mediated delivery SYTOX-Green. Error bars indicate standard error of the mean.

FIG. 4A. Viability effects on B16-F1 cells 4 hours after treatment with plasma.

FIG. 4B. Viability effects on HaCat cells 4 hours after treatment with plasma.

FIG. 5. Representative Xenogen images showing photon emissions per second acquired at day 2 for animals that received (A) no treatment, (B) injection of plasmid only, (C) plasmid with positive plasma treatment, (D) plasmid with positive plasma treatment and high impedance ring, (E) plasmid with positive plasma treatment, and (F) plasmid with negative plasma treatment and high impedance ring.

FIG. 6. Graph showing the daily mean photon flux (photons/s/$cm^2$) and standard error of the mean for animals that received (■) no treatment, (●) injection of plasmid only, (▲) plasmid with negative plasma treatment, and (▼) plasmid with negative plasma treatment and high impedance ring.

FIG. 7. Graph showing the daily mean photon flux (photons/s/$cm^2$) and standard error of the mean for animals that received (■) no treatment, (●) injection of plasmid only, (▲) plasmid with positive plasma treatment, and (▼) plasmid with positive plasma treatment and high impedance ring.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention includes a method and associated apparatus for the delivery of a molecule, typically a protein, plasmid or therapeutic drug, without the pain and damage associated with direct-contact electroporation applicators. The method and apparatus in accordance with the present invention are effective in using an electrical field to adjust the electrochemical potential of a target molecule thereby providing molecular transport of the target molecule into and/or across the tissue by a diffusive transport mechanism.

It may be appreciated by one of skill in the art that biological cells exist in many forms and in many types. In mammals, for example, there exist four basic types of cells: cells of epithelial, connective, muscle, and nervous tissue. The term cell, however, is to be broadly interpreted and the devices and methods described herein apply to all types of living cells including prokaryotes, eukaryotes and plant cells. In addition, the term cell also includes artificial cells such as liposomes and micelles. The term cell also has additional meaning which encompasses a single cell, cells in culture, cell aggregates, and a cell that is part of a tissue. Moreover, the term cell can also include a cell structure such as an intermembrane space, organelle or sub-cellular compartment.

The term tissue refers to a complex material which may include several types of cells. An illustrative tissue includes skin, including the epidermis (including the stratum corneum, lucidum, granulosum, spinosum and germinativum), dermis and/or hypodermis. Other tissues to which this method may be applied include, but are not intended to be limited to, tumor, skeletal muscle, smooth muscle, blood, blood vessel, brain, lymph, liver, pancreas, bone, colon, small intestine, cardiac, lung, breast, testes, prostate, and cornea. In a specific example, the present invention can be used for the transdermal delivery of a taget molecule. etc.

The term biological structure can include any cell, extra cellular matrix and/or tissue structure.

The term molecule, as used herein, refers to any type of molecular species. The devices and methods described herein are particularly applicable to therapeutic drugs, proteins, nucleic acid sequences, and plasmid DNA but can by applied to any type of molecule. In addition, the devices and methods are applicable for simultaneously affecting more than one type of molecule. Furthermore, the manipulation of these molecules and biological structures can be for the purposes of the enhancement of therapeutic molecule efficacy for the treatment of disease or for the prevention (such as vaccine) of disease.

The devices and methods described herein can be applied to any biological structure; either in vivo or in vitro. In addition to the use of this for combating disease, the instant invention can be used for research purposes. The devices and methods described herein can be used for diagnostic and/or molecular identification purposes.

The strength of the electric field, facilitates the delivery of a molecule to a target cell. For example, within some field strength ranges, the application time may be orders of magnitude longer than those previously described, although this is not intended as a limitation. For the purposes of this invention electric field is defined as the electric potential resulting from an ionic charge produced by an electrical conductor that is not in contact with the target cells. The ionic charge can be applied either a positive or negative plasma, that is a plasma generated by either a positive or negative voltage. Furthermore, both species of ions can be generated simultaneously by any of the devices and for any of the methods described in this document. The electric field may be applied constantly or in a manner that provides pulsed exposure to ionic charges. The magnitude and duration of the treatment with the electric field is dependent upon the particular combination of molecule(s) and cells(s) under investigation as well as the intended purpose of the applied charges.

Although a constant electric field applied for of a preferred embodiment employs ionized molecules, such as charged non-atmospheric gas (plasma) to create an electric field within a tissue; the following list of waveforms can be applied to the electrode/applicator to facilitate the creation of charge: square, rectangular, sinusoidal, radio frequency, triangular, alternating current, and any other waveforms that can be characterized by mathematical functions or mathematical approximations. In addition, these waveforms can be combined with a direct current bias (offset) or on combination with each other.

It is preferable in the use of plasmas in biological applications that the active species be generated at atmospheric pressure and temperature as not to cause thermal harm to cells or tissues. The non-thermal discharges may be generated by strong electric fields which accelerate ions toward an electrode. As these species travel toward the electrode they collide with other atoms or compounds in the gas phase to cause further ionizations. The ions may come from the surrounding atmosphere but are preferably provided by a non-atmospheric gas (i.e. helium, argon, nitrogen or combination thereof).

In one embodiment, the characteristics of the potential used to generate plasmas to facilitate the entry of the molecules into the biological structure is between about +8 kV and about −8 kV. The plasma treatment of this embodiment may comprise a single pulse ranging from about 2 minutes to 20 minutes in duration that results in the driving potential in the preferred embodiment. A single pulse of substantially continuous energy may be applied or a plurality of sequential pulses, either of the same magnitude or differing magnitudes of duration and applied potential to generate plasma and ultimately include an electric field in/near/in the vicinity of target cells and tissues. In fact, the potential needed to effect facilitation of molecular delivery may be significantly lowered using longer pulse durations. As a result, fewer deleterious effects of the procedure are experienced, since the electric field imposition is more a function of time rather than field strength. The magnitude of the electric fields applied are selected based on the susceptibility of the particular tissue to the pulses, and the corresponding pulse durations are a function of the resistivity of the type of tissue to temporary electrical damage.

EXAMPLE I

Figure 1:
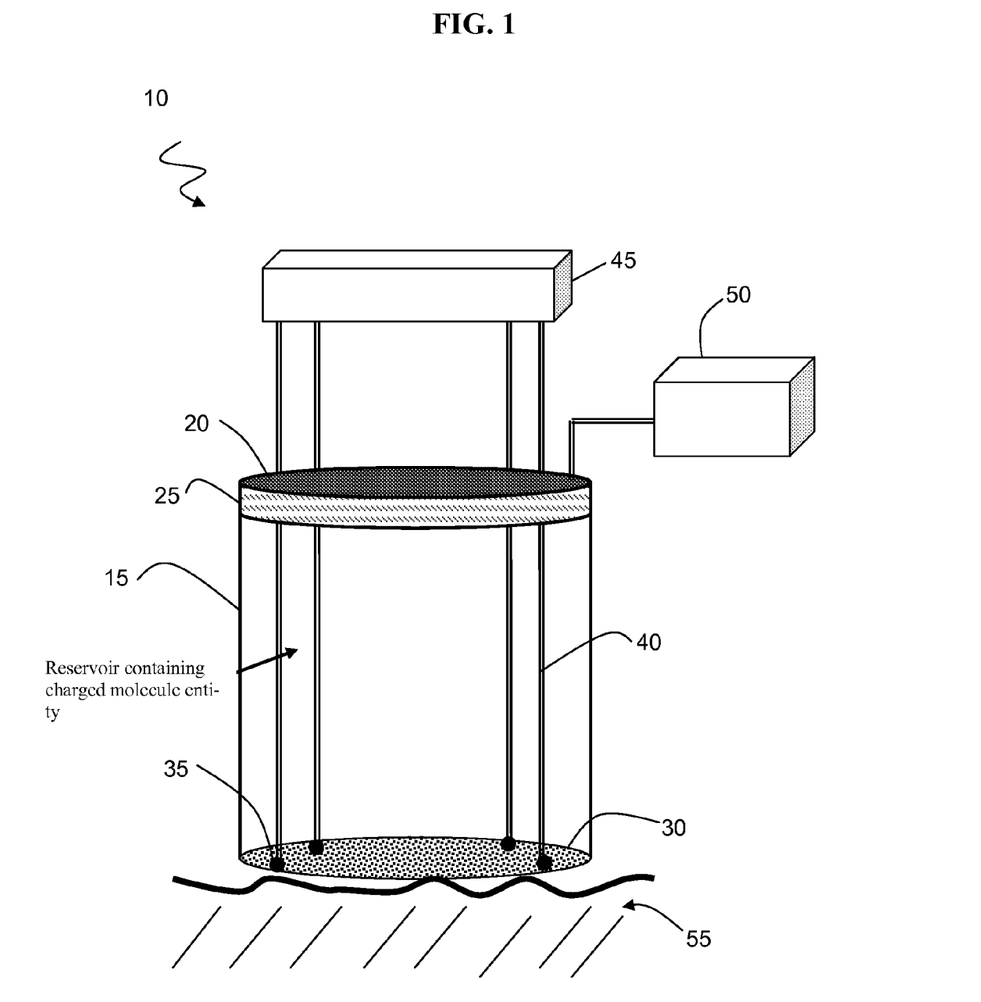

With reference to FIG. 1, in one embodiment, electric field generation device 10 includes top end cap 20, a volumetric containment vessel or reservoir 15 and a bottom end cap 30. Top end cap 20 is constructed of a material with the appropriate dielectric properties to assure that it will hold a charge sufficient to polarize charged entities contained within the volumetric vessel 15. Accordingly, the top end cap could be a stainless steel frit or fabricated from a variety of other semi-conductive materials known in the art. Materials with such dielectric properties that can be machined or molded to the required top end cap 20 are readily available in the art. The reservoir 15 is preferably fabricated from a non-conductive material that is impervious to the change entity or target molecule being stored. As such, the reservoir may be fabricated of a polymeric or a variety of other nonconductive materials known in the art. The bottom end cap of the reservoir 30 is fabricated of a micro-porous material or microporous membrane. Appropriate materials for the reservoir walls 15, the micro-porous membrane 30 and the conductive top end cap 20 are commercially available and known in the art.

To insulate the conductive top end cap 20 from the reservoir 15, an insulative seal 25 is positioned between the top end cap and the reservoir.

Polarization voltages are delivered to the top end cap 20 by a polarization voltage supply 50. Various means are envisioned to provide the electrical connection from the supply to the cap, including an electrical polarization tab integral to the surface of the top end cap.

The bottom end cap 30 further includes a plurality of electroporation applicators 35. These electroporation applicators may be embedded within the micro-porous material of the end cap 30, or otherwise secured by means known in the art. Each of the electroporation applicators 35 is in circuit communication with a source of electroporation voltage 45 through a plurality of conductive leads 40. The source 45 is capable of providing a variety of voltage application protocols. Additionally, the electroporation applicators 35 may be driven independently or in combination, for the application of the electroporation treatment as necessary by the particular application of the device. The conductive leads 40 connecting the electroporation applicators 35 to the source 45 may pass through the top end lid 20. Accordingly, the top end cap 20 may include electrical through-puts to insulate the leads 40 from the conductive top cap 20.

EXAMPLE II

A method in accordance with the present invention utilizes the combination of diffusion and electroporation. In a preferred embodiment, when a charge is placed on the top end cap 20 of the device 10, the charged entity within the vessel 15 will respond to that charge and move within the vessel accordingly. If the applied polarization charge on the top end cap 20 forces the charged entity within the vessel to migrate to the micro-porous membrane 30 at the bottom of the reservoir, this action will increase the chemical potential across the membrane and facilitate transport of the charged entity from the reservoir 15 through the porous membrane 30 and into the target tissue 55. After the transfer of the desired molecules into the target tissue 55, an appropriate electroporation protocol is initiated utilizing the electroporation applicators 35 imbedded in the bottom end cap 30 of the device 10. The electroporation protocol is effective in introducing the target molecule or charged entity into the cells of the target tissue 55.

EXAMPLE III

Figure 2A:
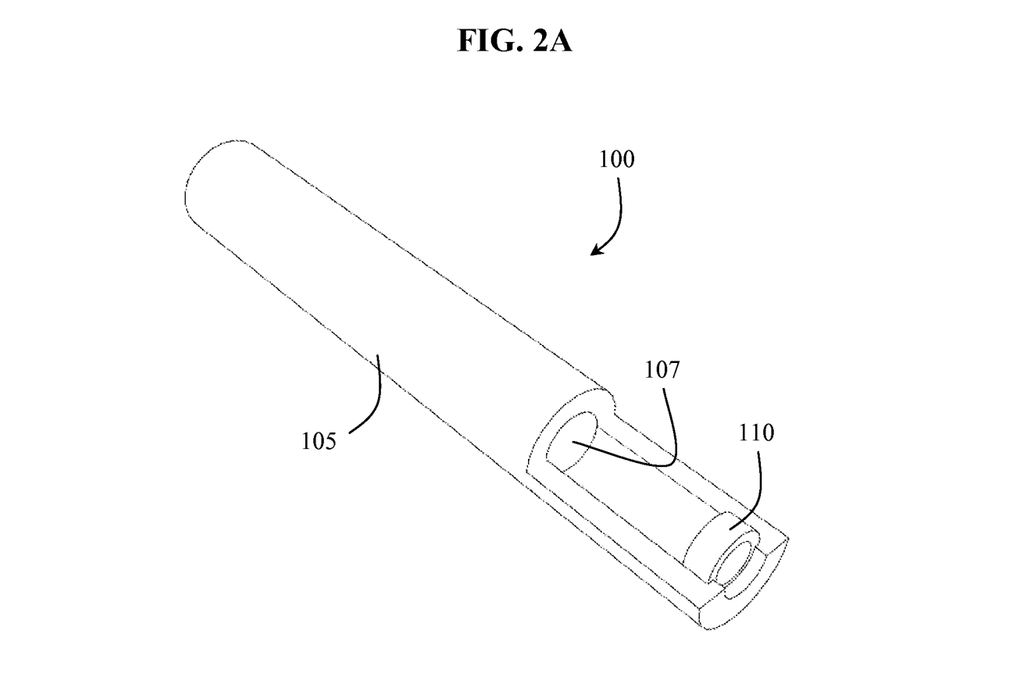

Referring now to FIG. 2A, electric field generation device 100 includes tube 105 having inner channel 107. In an illustrative embodiment, tube 105 is approximately 15 cm long and the diameter of inner 107 is approximately 1 cm. Annular electrode 110 is positioned substantially at the opening of tube 105. Tube 105 is connected to a high-voltage and low-current direct current power supply (not shown). In this embodiment, an electric potential of about +8 kV or −8 kV is applied to electrode 110 depending on the desired polarity. A stream of ultra high purity helium is passed through inner channel 107 and electrode 110 at a rate of 15 l/min.

Figure 2B:
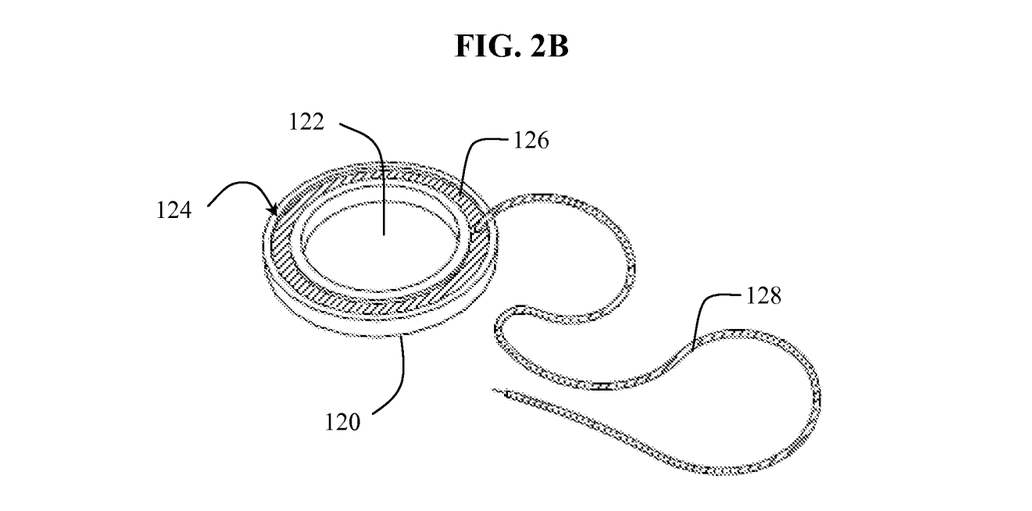

In another embodiment, shown in FIG. 2B, device 100 (not shown) is used conjunction with sample plate 120. Plate 120 further comprises inner chamber 122 and outer chamber 124. Inner chamber 122 is adapted to hold a biological structure, such a cell sample. Outer chamber 124 is adapted to received grounding ring 126 which is connected to ground through wire 128. Grounding ring 126 and wire 128 can be made from any conductive material, as is known in the art. In yet another embodiment, wire 128 passes through a high impedance. It is contemplated, however, that grounding ring 126 can be placed directly on the surface of the biological structure. In transdermal drug delivery applications, for example, grounding ring 126 may be temporarily placed directly on the skin (as with a mild adhesive).

Various ion sources (gases) were tested in constructing electric field generating device 100, including argon, nitrogen, and helium. To perform these tests the device was placed 2 cm above a grounded metal plate. A flow of argon, nitrogen, or helium was passed through the tube at 10 l/min, while the voltage was raised until a discharge was visible and further raised to a point where sparking occurred. It is preferable for the ion source to have a low breakdown voltage and require a high voltage to arc to the plate. However, gases become more conductive in their ionized states, which causes them to arc at slightly higher voltages than the breakdown potential. Nitrogen was readily broken down at 3.5 kV, argon followed at 4 kV and helium at 6.5 kV. From this helium was chosen as it required a slightly higher change in voltage to arc to the plate and sparks were much less frequent with this gas as compared to the others.

The device, using helium as the ion source, was raised 10 cm away from the bench top and the operating parameters were changed to produce the longest possible visible plume. A longer plume is desirable as it allows the device to be operated further from the treatment site. Creating a stable plume using ultra-pure helium (99.999% He) with this system required a helium flow rate of 15 l/min at atmospheric pressure and the electrode be operated at 8 kV for either polarity. Under these conditions a 27 mm plume was visible for positive polarity and 20 mm for negative polarity.

EXAMPLE IV

To demonstrate the plasma generator was capable of inducing delivery, a series of in vitro experiments was performed. These experiments focused on delivering the live cell impermeant nucleic acid stain SYTOX-Green to the cell interior. Once inside a cell, SYTOX-Green binds with nucleic acids causing a 500-fold increase in fluorescence. Resulting fluorescence levels were analyzed using a microplate spectrofluorometer. Prior to performing these experiments a dose-response relationship was expected with respect to plasma exposure time, where those cells treated for longer times would exhibit higher levels of fluorescence than those treated with lower doses. It should also be noted that higher fluorescence levels could indicate either a greater degree of delivered SYTOX-Green or overexposure leading to cell death.

The SYTOX-Green experiments were carried out in tissue culture dishes, which are two-chambered dishes. During the treatments the inner chamber contained $1 \times 10^6$ murine melanoma (B16-F10) cells suspended in 500 µl of PBS. The outer chamber contained a ring that ran through a resistive load of 1.5 GΩ to ground potential. This ring was necessary to prevent the polystyrene dish from charging too quickly, causing the plasma plume length to shrink thereby reducing overall delivery efficiency. Treatments exposed the center well to plasma derived from +8 kV for 0, 120, 300 or 600 seconds. The height of the plasma generator was determined by the distance at which the tip of the visible plasma plume touched the cell solution in the inner well. For positive polarity this distance was 27 mm. After the plasma exposure was completed 500 µl of 2 µM SYTOX-Green was added to the suspension in each dish. Next, the cells were incubated at 37° C. for 30 minutes. After incubation, fluorescence levels were quantified.

Figure 3A:
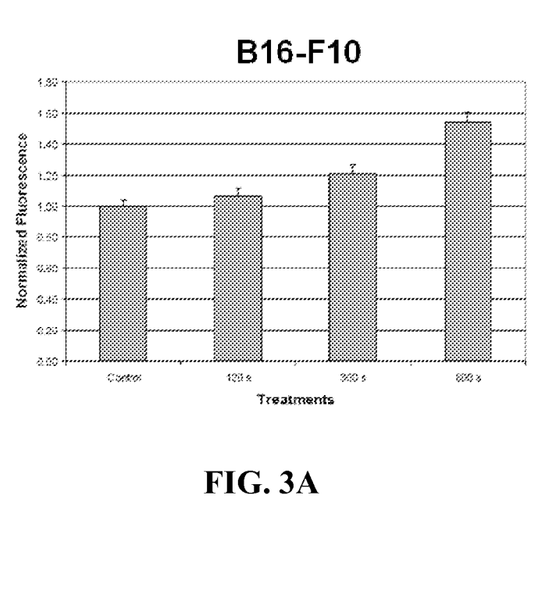
Figure 3B:
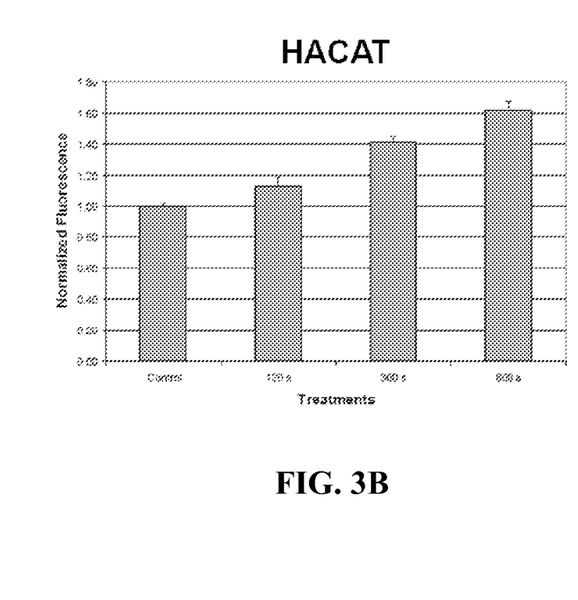

Each set of treatment conditions was performed a total of three times per experiment, and each experiment was performed a total of three times. FIG. 3A shows the resulting mean data. Statistical analysis indicated that with a 95% confidence level the fluorescence of both 300 and 600 s exposure times were greater than the fluorescence of control samples (exposure to Sytox-Green but no plasma treatment). An identical set of experiments was performed using human keratinocytes (HaCat) with almost identical results. FIG. 3B show the mean fluorescence data for these experiments. This indicated a membrane permeabilization event had occurred that followed a dose-response behavior, but did not indicate if the event was reversible or terminal.

EXAMPLE V

Figure 4A:
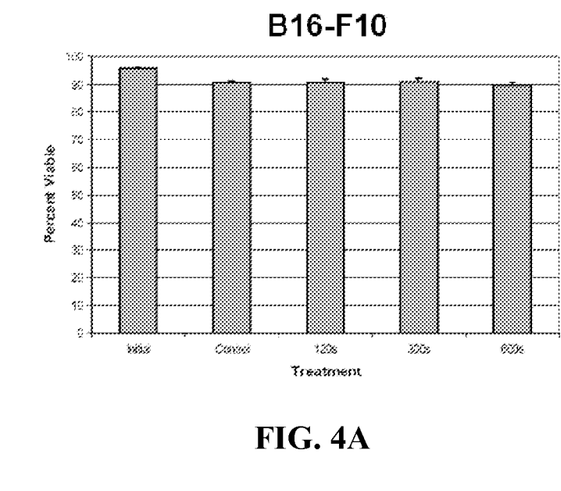
Figure 4B:
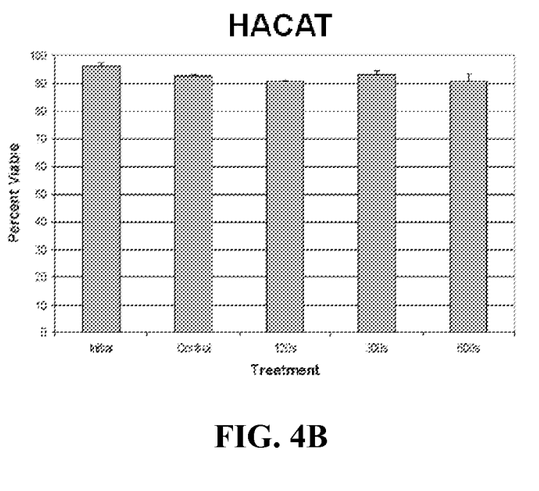
Figure 5:
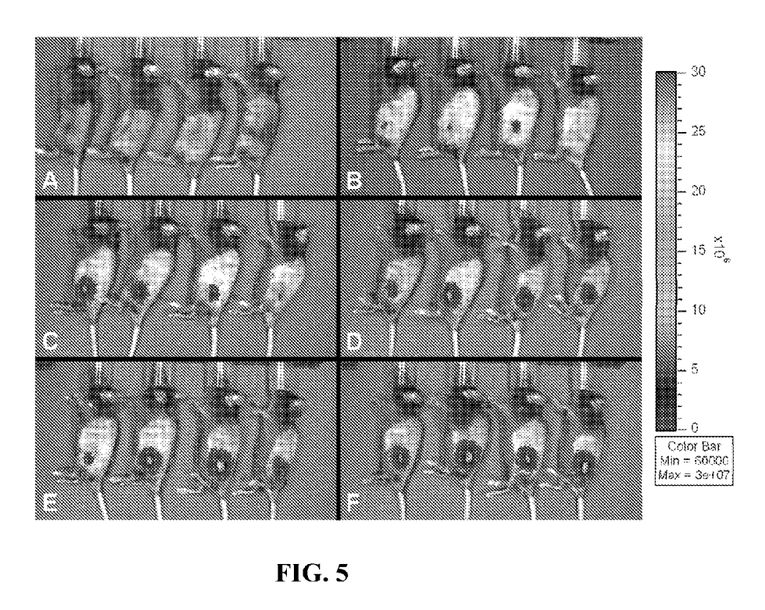

To determine the impact plasma exposure has on viability a second set of experiments was carried out. In these experiments initial viability was obtained with a trypan blue assay prior to cells being placed into dishes for treatment. A total of twelve dishes were filled with $1 \times 10^6$ B16-F10 cells suspended in 500 µl of McCoy's media. Sets of three dishes were divided into the following groups: a control group that received no treatment; 120 s positive plasma exposure; 300 s positive plasma exposure; and 600 s positive plasma exposure. The outer chamber of the dishes treated with plasma contained a ring that ran through a resistive load of 1.5 GΩ to ground potential. After the plasma exposure was completed the cells were incubated at 37° C. in 5% $CO_2$ for 4 hours. Following incubation the viability was ascertained using a trypan blue assay. Three counts were taken per sample and treatments were conducted three times in each experiment. For statistical accuracy experiments were repeated a total of three times. Mean data for these experiments are shown in FIG. 4A. Analysis of the data from these experiments proved at the 95% confidence level that each plasma treatment conducted did not cause a decrease in the viability when compared to untreated cells. These experiments were also conducted on HaCat cells which showed similar results (FIG. 4B). This indicates that any level of plasma induced permeabilization of cell membranes is a transient event and plasma exposure does not harm short term viability.

EXAMPLE VI

The following example illustrates the ability of the invention deliver plasmid DNA to a target tissue. This example clearly shows the application of a stream of charge in the form of plasma deposited on a tissue surface can augment the uptake of plasmid DNA infused into those tissues. In contrast to other physical delivery methods available for molecular delivery, this method does not rely on intimate contact of the applicator with the treatment site. As it can be seen, non-thermal plasma can achieve as much as 732% higher expression when compared to injection of plasmid DNA only. This delivery likely occurs due to the constant deposition of charged species on the treatment site. While the deposition of charged species on the surface of the skin increases the uptake of macromolecules it does not cause damage to the skin, which makes it an attractive technique.

Murine Model

Female C57BL/6 mice (NIH, Bethesda, Md.) were 6-7 weeks of age at the beginning of the study. All animals were humanely euthanatized at the conclusion of the study in accordance with an approved Institutional Animal Care and Use Committee protocol.

Anesthesia

Prior to treatment mice were placed in a plexiglass induction chamber and anestisized with a constant supply of constant supply of 2% isoflurane in oxygen mixture (Caliper Life Sciences, Hopkinton, Mass.). After the mice had been induced the treatments were carried out using a constant supply of 2% isoflurane delivered by a nose cone, this effectively maintained a level anesthesia plane throughout treatment. Animals were placed on a 32° C. warming pad to prevent heat loss caused by the disruption of thermoregulatory mechanisms associated with anesthesia induction.

Treatments

This study consisted of treating six different groups with luciferase encoding plasmid and helium plasma to examine the utility of the charge source to enhance DNA delivery. All plasmid injections were performed using a 1 cc syringe with a 30 gauge needle (BD, Franklin Lakes, N.J.). A 50 µl injection containing 0.1 mg gWIZ luciferase plasmid in saline (Aldevron, Fargo, N. Dak.) was injected intradermally for all animals that received DNA.

Groups of 4 animals were treated in the following manners: no treatment (not injected with plasmid and no exposure to plasma); luciferase plasmid injection with no exposure to helium plasma; plasmid injection and exposure to positive plasma for ten minutes; plasmid injection and exposure to negative plasma for ten minutes; plasmid injection and exposure to positive plasma for ten minutes with a high impedance ground ring encircling the treatment area; and plasmid injection followed by exposure to negative plasma for ten minutes with a high impedance ground ring encircling the treatment area. This experiment was conducted a total of three independent times.

Luminescence Quantification

Luciferase expression was determined by injecting 150 mg/kg of body weight D-luciferin (Caliper Life Sciences, Hopkinton, Mass.) intraperitoneally in anestisized mice. After injection a light producing reaction occurs from the oxidation of luciferin, which is facilitated by the presence of the luciferase enzyme. Light emissions caused by this reaction were captured 15 minutes after injection by placing the anesthetized animals in a Xenogen IVIS 200 series imaging system (Caliper Life Sciences, Hopkinton, Mass.). The photon flux (photons/s/$cm^2$) of these emissions was calculated using Living Image software (Caliper Life Sciences, Hopkinton, Mass.). Luminesence data was gathered at days 0, 2, 4, 6, 8, 10, 18 and 26.

Statistical Analysis

After all data was gathered the mean and standard error for each treatment group was calculated for identically treated groups on each of the follow-up days. From these data, a two-sided studentized t-test was performed with a 95% confidence level between treatment groups for each day data was collected. This allowed conclusions to be reached concerning the relative amounts of expressed luciferase.

Results

As previously discussed, a helium flow rate of 15 l/min was necessary to sustain a reproducible glow discharge when operating the annular electrode at an applied potential of +8 kV or −8 kV and 10 µA. Operating at these conditions the ionized gas stream produced a glow approximately 3.5 cm in length emanating from the annular electrode. Temperature measurements made with an infrared thermometer (Fluke Model 62, Everett, Wash.) at 0.5 cm intervals along the length of the 3.5 cm plume showed no deviations in temperature from that of the unexcited gas alone. Voltage on the surface of the skin immediately below the center of the plasma treatment site was 4 kV. At 1 cm away from the center of the treatment site the voltage was 1 kV. These values on the skin allow substantial voltage drops across the skin layers due to the high permittivity of skin and relatively low permittivity of muscle and blood beneath.

Exposing animals to plasma created at these conditions caused no muscle contractions, no visible damage to the skin, and no abnormal skin growth throughout the 26 day follow-up period.

FIGS. 5A through 5F shows Xenogen images from animals treated at representative time points in the 26 day follow-up period. Images A and B in the figure are from day 2 of the follow up period for animals that received no treatment and an injection of plasmid encoding luciferase, respectively. Note that there is some luminescence that resulted from injection of the plasmid only. Image C is from day 2 from animals that received plasmid followed by positive plasma treatment for 10 minutes; Image D was taken on the same day from animals that received positive plasma treatment with the ground ring. Similarly, images E and F were taken on day 2 and were from animals that received plasmid with negative plasma (E) and plasmid with negative plasma treatment that included the ground ring (F). Each of the four treatments involving exposure of the injection site to plasma appear to have increased expression relative to animals that received only an injection of luciferase encoding plasmid.

Figure 6:
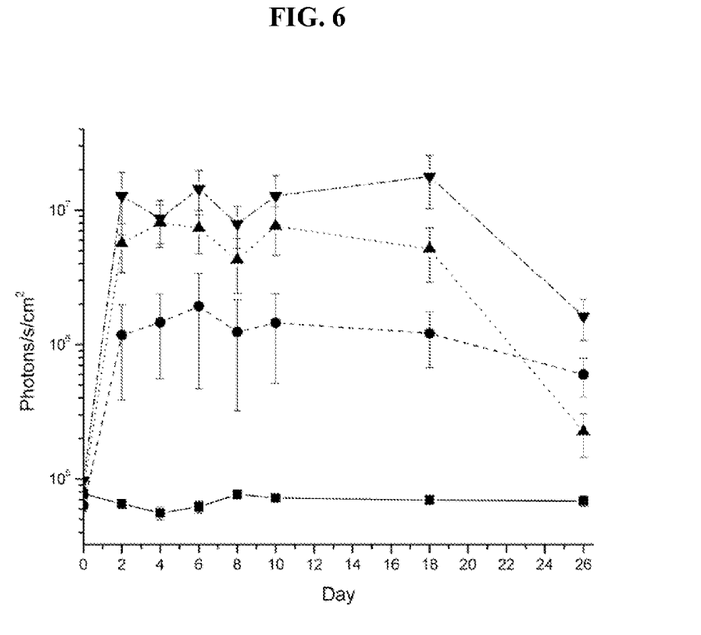
Figure 7:
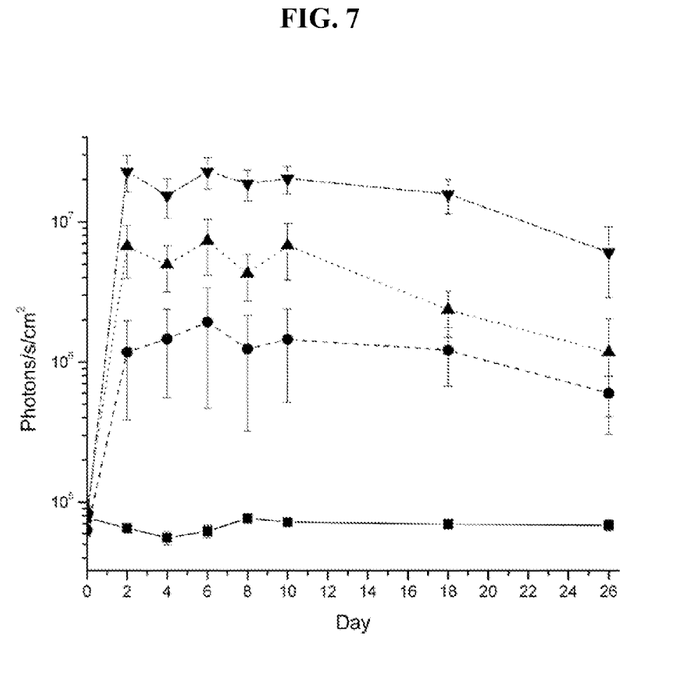

Mean quantitative luciferase level data for all groups over the 26 day follow-up period is shown in FIG. 6 for animals treated with negative polarity helium plasma and FIG. 7 for those treated with positive polarity helium plasma. These plots show all treatment groups starting out at background luminescence levels. Two days after treatment the groups injected with luciferase plasmid peaked at their maximum expression levels, where they remained until day 18 when luminescence began to decrease. Comparisons relative to the injection-only group indicated a rise of: 180% with exposure to positive plasma; 245% to negative plasma; 691% to positive plasma with a high impedance ring encircling the treatment site; and 732% to negative plasma with a high impedance ring encircling the treatment site.

Statistical analysis was performed between groups using a two sided t-test having 95% confidence. This analysis showed exposure to ionized gases of either polarity is capable of increasing the uptake of macromolecules delivered to the dermis relative to animals that received only an injection of plasmid DNA. Further, the analysis showed a statistically significant difference between the groups that received DNA followed by either helium plasma produced by negative polarity or positive polarity helium plasma with the high impedance ground ring placed around the treatment site. Conversely, there was no statistical difference between the two groups that received DNA followed by positive polarity plasma and DNA combined with positive polarity and a ground ring. However, there was insufficient statistical evidence in the groups exposed only to helium ions alone (no ground ring) to suggest that either polarity was more efficacious.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A non-contact, charge-based method of facilitating the movement of a molecule relative a biological structure, comprising:
    positioning the molecule adjacent the biological structure;
    providing an electric field generating device having at least one electrode;
    providing an ion source in fluid communication with the electrode wherein the ion source is a gas selected from the group consisting of argon, nitrogen, helium, atmospheric gases and combinations thereof;
    positioning the electric field generating device proximate to the biological structure;
    applying a first potential to the electrode wherein the first potential is established using direct current (DC) wherein the first potential is between about +8 kV and about −8 kV;
    establishing a substantially continuous, low-level electric field by flowing the ion source past the electrode to generate a plasma; and
    establishing a second potential by depositing plasma ions on the biological structure whereby the establishment of the second potential on the biological structure is capable of moving the molecule relative to the biological structure;
    wherein the plasma is applied to the biological structure for at least 2 minutes.

2. The method of claim 1, further comprising the step of applying a bias potential to the biological structure.

3. The method of claim 1, wherein the electric field facilitates the movement of the molecule through a permeable membrane into the biological structure.

4. The method of claim 1, wherein the electric field facilitates the movement of the molecule through a permeable membrane out of the biological structure.

5. The method of claim 1, wherein the first potential is a positive DC voltage.

6. The method of claim 1, wherein the first potential is a negative DC voltage.

7. The method of claim 1, wherein the plasma is applied to the biological structure substantially continuously from about 2 minutes to about 20 minutes in duration.

8. The method of claim 1, wherein the ion source is substantially pure helium.

9. The method of claim 8, wherein the ion source is flowed past the electrode at a rate of about 15 l/min.

10. The method of claim 1, wherein the plasma is selected from the group consisting of a positive plasma, a negative plasma, or combinations thereof.

11. The method of claim 1, further comprising providing a ground ring around the biological structure.

12. The method of claim 1, wherein the plasma is non-thermal.

13. The method of claim 1, further comprising providing a conductive path to ground in electrical contact with the biological structure.

14. The method of claim 13, wherein the conductive path to ground passes through an impedance that is in electrical contact with the biological structure.

15. The method of claim 13, further comprising a conductive material connected to ground that is in electrical contact with the biological structure.

16. The method of claim 1, wherein the molecule is positioned on the surface of the biological structure.

17. The method of claim 1, wherein the electric field generating device is positioned up to about 10 cm from the biological structure.

18. The method of claim 1, wherein the molecule is injected into the biological structure.

19. The method of claim 1, further comprising providing a second biological structure within the biological structure.

20. The method of claim 19, wherein the electric field facilitates the movement of the molecule through the biological structure and into the second biological structure.

21. The method of claim 19, wherein the electric field facilitates the movement of the molecule out of the second biological structure and into the biological structure.

22. The method of claim 1, wherein the molecule is a drug, DNA, RNA, plasmid DNA, nucleic acid, antibody, protein or polypeptide.

23. A non-contact, charge-based method of facilitating the movement of a molecule relative a biological structure, comprising:
- positioning the molecule adjacent the biological structure;
- providing a plasma generating device having at least one electrode and an ion source wherein the ion source is in fluid communication with the at least one electrode;
- positioning the plasma generating device proximate to the biological structure;
- establishing a plasma in proximity to the biological structure wherein direct current (DC) is used to establish the plasma;
- applying the plasma to the biological structure wherein the plasma is applied to the biological structure for a substantially continuous period of time of at least about 2 minutes; and
- depositing ions on the biological structure to establish a potential wherein the deposition of the ions is effective in moving the molecule relative to the biological structure.

24. The method of claim 23, wherein the ion source is a gas selected from the group consisting of argon, nitrogen, helium, atmospheric gases and combinations thereof.

25. The method of claim 23, wherein the ion source is substantially pure helium.

26. The method of claim 23, wherein the plasma is non-thermal.

27. The method of claim 23, wherein the plasma is applied to the biological structure for between about 2 minutes and about 20 minutes.

28. The method of claim 23, further comprising providing a ground ring around the biological structure.

29. The method of claim 23, further comprising providing a conductive path to ground in electrical contact with the biological structure.

30. The method of claim 29, wherein the conductive path to ground passes through an impedance that is in electrical contact with the biological structure.

31. The method of claim 29, further comprising a conductive material connected to ground that is in electrical contact with the biological structure.

32. The method of claim 23, wherein the molecule is positioned on the surface of the biological structure.

33. The method of claim 23, wherein the molecule is injected into the biological structure.

34. The method of claim 23, wherein the plasma is selected from the group consisting of a positive plasma, a negative plasma, or combinations thereof.

* * * * *